United States Patent
Eyal

(12) 
(10) Patent No.: US 6,169,187 B1
(45) Date of Patent: *Jan. 2, 2001

(54) PROCESS FOR RECOVERY OF ASCORBIC ACID

(75) Inventor: Aharon Meir Eyal, Jerusalem (IL)

(73) Assignee: Yissum Research Development Company of the Hebrew University of Jerusalem, Jerusalem (IL)

( * ) Notice: Under 35 U.S.C. 154(b), the term of this patent shall be extended for 0 days.

This patent is subject to a terminal disclaimer.

(21) Appl. No.: 09/319,141

(22) PCT Filed: Nov. 25, 1997

(86) PCT No.: PCT/US97/22395

§ 371 Date: Aug. 9, 1999

§ 102(e) Date: Aug. 9, 1999

(87) PCT Pub. No.: WO98/24777

PCT Pub. Date: Jun. 11, 1998

(30) Foreign Application Priority Data

Dec. 1, 1996 (IL) .......................................... 119732

(51) Int. Cl.[7] ...................... C07D 307/32; C07D 307/33; C07C 209/86
(52) U.S. Cl. ........................... 549/315; 549/316; 564/394; 564/438
(58) Field of Search ................................... 549/315, 316; 564/394, 438

(56) References Cited

U.S. PATENT DOCUMENTS 4,275,234 * 6/1981 Baniel et al. ........................ 562/584
4,778,902 10/1988 Fujiwara et al. ..................... 549/315
4,994,609 * 2/1991 Baniel et al. ........................ 562/580
5,041,563 8/1991 Fahrni et al. ........................ 549/315

FOREIGN PATENT DOCUMENTS

0133493 * 2/1985 (EP) .
1 426 018 2/1976 (GB) .
WO96/38433 12/1996 (WO) .

OTHER PUBLICATIONS

Caplus DN 103:178578 ; Fahrni et al , Abstract, Feb. 27, 1985.*

* cited by examiner

Primary Examiner—Alan L. Rotman
Assistant Examiner—Rita Desai
(74) Attorney, Agent, or Firm—Williams, Morgan & Amerson, P.C.

(57) ABSTRACT

The invention provides a process for the recovery of ascorbic acid from a feed containing at least one precursor of ascorbic acid comprising converting the precursor into at least one product, the at least one product being ascorbic acid in an organic extractant composition, the organic extractant composition comprising at least one secondary or tertiary alkyl amine in which the aggregate number of carbon atoms is at least 20, as a primary extractant, and a polar extraction enhancer compound; wherein the extractant composition comprises at least 2 moles of the polar extraction enhancer compound per one mole of primary extractant; and subjecting the ascorbic acid-containing organic extractant composition to a stripping operation with aqueous solution at a temperature of at least 20° C. higher than the temperature at which the conversion is carried out; whereby there is obtained an aqueous solution of ascorbic acid in which the concentration of ascorbic acid is higher than 5%.

28 Claims, No Drawings

PROCESS FOR RECOVERY OF ASCORBIC ACID

This application is a 371 of PCT/US97/22395 filed Nov. 25, 1997.

The present invention relates to a process for the production of ascorbic acid. More particularly, the present invention relates to the recovery of ascorbic acid from a feed solution containing at least one precursor of ascorbic acid, wherein the term precursor of ascorbic acid as used herein is intended to denote compounds that can be converted to ascorbic acid in only a few process steps, as described hereinafter, e.g., compounds selected from the group consisting of salts of ascorbic acid, 2-keto-L-gulonic acid in acid and salt form and derivatives thereof.

As described, e.g., in Kirk-Othmer's *Encyclopedia of Chemical Technology*, Third Edition, ascorbic acid (L-ascorbic acid, L-xylo-ascorbic acid, L-threo-hex-2-enonic acid g-lactone) is the name recognized by the IUPAC-IUB Commission on Biochemical Nomenclature for vitamin C. The name implies the vitamin's antiscorbutic properties, namely, the prevention and treatment of scurvy. L-ascorbic acid is widely distributed in plants and animals. The pure vitamin ($C_6H_8O_6$, mol. wt. 176.13) is a white crystalline substance derived from L-gulonic acid, a sugar acid, and synthesized both biologically and chemically from D-glucose.

Although natural and synthetic vitamin C are chemically and biologically identical, in recent years a limited amount of commercial isolation from vegetable sources, e.g., rose hips, persimmon, citrus fruit, etc., has been carried out to meet the preference of some persons for vitamin C from natural sources. L-ascorbic acid was the first vitamin to be produced in commercial quantities, and manufacture is based on the well-known Reichstein and Grussner synthesis, which involves the steps of hydrogenation of D-glucose to D-sorbitol; fermentation (oxidation) to L-sorbose; acetonation to bis-isopropylidene-α-L-sorbofuranose; oxidation to bis-isopropylidene-2-oxo-L-gulonic acid, and hydrolysis, rearrangement and purification to L-ascorbic acid.

A fermentation of a carbohydrate to ascorbic acid or to a precursor thereof would be very attractive, saving on operations and on expensive reagents, in addition to its being derived from a natural fermentation process, as opposed to a synthesis involving chemical steps. There are indications that such fermentation route to ascorbic acid is feasible. Yet fermentative industrial production of ascorbic acid faces two major difficulties: (a) the product concentration in the fermentation medium is low; and (b) said product is at least partially a precursor of ascorbic acid rather than the ascorbic acid in its free acid form.

Conversion of said precursor to ascorbic acid and purifying the ascorbic acid by conventional methods without introduction of energy as a driving force would result in a purified product of concentrations similar to those in the feed. Due to its high solubility in water, the cost of ascorbic acid crystallization by water evaporation would be prohibitive. The presence of ascorbate acid precursor, rather than the acid or in addition to it, presents the following two problems: (a) for various applications the acid form of the product is desired, and (b) separation of the precursor, particularly if an ascorbic salt, is more difficult than separation of the acid as separation methods available for salts are usually less selective and of lower yields. Thus, recovery of ascorbic acid from a feed solution comprising a precursor thereof is at present difficult, particularly when the overall precursor concentration in said feed is low. Such feed could result from various sources, such as fermentation to ascorbic acid or to a precursor thereof or from other production process. Those could also be a result of removing ascorbic acid from a feed consisting initially of the acid and its precursor.

Several methods were proposed for combining purification of carboxylic acids with their concentration. In the case of citric acid, it is achieved by the addition of lime to crystallize calcium citrate, which has very low solubility in water. This salt is separated, washed and acidulated with sulfuric acid. Purified and concentrated citric acid is obtained. This method is not applicable for ascorbic acid, as its alkali and alkali earth salts are highly soluble.

A process was proposed in which carboxylic acids were extracted and then displaced from the extractant by a solution of concentrated mineral acids. Both liquid (long chain amines) and solid (resins carrying amine groups) anion exchangers could be considered for this purpose. The purity of the displaced carboxylic acid depends on the preference of the extractant to the mineral acid. Such a process might be applicable for ascorbic acid separation and concentration, provided that the extractant is strong enough to reach high extraction yield, that it shows high preference to the displacing acid, and that the ascorbic acid is stable at the high acidity of the displacing solution.

The regeneration of the anion exchanger would require neutralization by a base. Using HCl as the displacing acid and distilling it of the extractant was proposed, but the high temperatures required and the extractant's decomposition at these conditions are prohibitive. If the anion exchanger is represented by B, the ascorbic acid in the feed solution and in the pure form are $AA_F$ and $AA_P$, respectively, the displacing acid is HCl, and the neutralizing base is NaOH, the equations of the process stages and of the overall reaction are as follows:

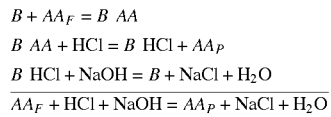

Reagents are consumed, and a by-product salt of no (or negative) value is produced.

Many methods were suggested for the conversion of anions of salts into the acid form. An example for such conversion method is contacting said aqueous solution containing said salt with a water immiscible cation exchanger in its acid form, which cation exchanger could be in solid form, e.g. a resin, or liquid, e.g. a water immiscible organic acid. On such contact cations from said aqueous solution are adsorbed on or extracted into the said water immiscible cation exchanger and protons are transferred into said aqueous solution where they combine with the anions to form the free acid. The cations carrying cation exchanger is then regenerated with an acid, which results in consumption of more than one mole of said regenerating acid per mole of acid to be converted and formation of more than one mole of an undesired salt.

Preferably, said conversion is effected in a method that does not consume acids and bases as reagents and does not reject salts into the environment. Such methods, also termed salt splitting, convert the salt into the corresponding acid and a basic compound of the cation. Such basic compound is typically hydroxides, bicarbonates and carbonates. Separation of these two products is desired so that at least one of those is transferred into another phase. Preferably, both products are transferred into another phase and separated thereby from impurities present in the feed solution. The acid could be distilled out, if volatile, extracted into a water immiscible extractant or bound to a basic solid adsorbent. The basic compound of the cation could be crystallized out, if of low enough solubility or bound to an adsorbent. The two products could also end up in two aqueous solutions separated by a membrane. All these options suffer from a common problem. During the conversion step the phases consisting of the product acid or the product basic compound of the cation are in contact with the feed solution and thereby the two products could react back to the salt. Thus, in order to effect the conversion, at least one of the products needs to be continuously removed. An attractive solution could be extraction of the acid as it forms, or extraction of the anion of the acid and the protons formed on this conversion into an extractant and formation of the product acid therein (based on the available know how on acid extraction, these two cases are not easily differentiated, at least for some of the acids). Such extraction provides for the purification of the product as well as for its separation and for the facilitating of the conversion.

Using a relatively weak extractant would result in an extract (organic phase consisting of the extracted acid), which is relatively dilute in the product. Thus, back-extraction with water to recover the product therefrom in an acid form would also result in a diluted product solution. On the other hand use of a strong extractant is undesirable, as back-extraction of the acid therefrom (in an acid form) would result in too-diluted a product.

Thus, in King's U.S. Pat. No. 5,132,456, a strongly basic extractant extracts part of the lactic acid from the neutral solution, which results in a lactic acid loaded extractant and a basic solution, which could be recycled as a neutralizing medium to the fermentation. The difficulty with such strong extractant is that it holds strongly to the extracted lactic acid. Recovery of the extracted acid by stripping with water results in a too dilute product (back-extract).

U.S. Pat. No. 5,132,456 suggests a way for recovering extracted carboxylic acid from a strong extractant. It comprises leaching or back-extraction with an aqueous solution of ammonia or low molecular weight alkylamine, especially trimethyl amine (TMA). The resultant aqueous ammonium or alkylammonium carboxylate solution can be concentrated if necessary, and the carboxylate can be decomposed thermally to yield the product carboxylic acid and ammonia or amine which can be condensed and recycled. This process is costly and complex and gives room for undesired reactions as well as for thermal decomposition, to which ascorbic acid is particularly sensitive.

In 1976, there issued British Patent 1,426,018 and in 1981 there issued the corresponding U.S. Pat. No. 4,275,234, directed to the recovery of acids from aqueous solutions. In said patents, there are exemplified the recovery of citric acid, lactic acid, oxalic acid, and phosphoric acid from an aqueous solution of the same acid; in fact, said U.S. Patent is specifically limited in its claims to the recovery of one of said four acids.

If the conversion step in the present invention is viewed as being analogous to a step of subjecting the aqueous solution to extraction in said aforementioned patent, then the present invention as defined herein may be considered as formally falling within the scope of said aforementioned British patent, the relevant teachings of which are incorporated herein by reference, and in this sense the present invention may be viewed as constituting a selection therefrom. However, as will be explained further below, not only do said patents neither teach, suggest, nor exemplify the applicability of said process to the recovery of ascorbic acid from a feed containing a precursor thereof, but in fact, from a careful analysis of said patents, one would not expect said process to be feasible for the recovery of ascorbic acid, as is also evidenced by the fact that twenty years have passed from the publication of said British patent without any person skilled in the art either suggesting or applying said process to ascorbic acid recovery from said feed.

Referring now to said patents and the teachings thereof, one finds that the process taught therein utilizes the effect of temperature on phosphoric and carboxylic acid extraction by amine-based extractants. The term "amine" as used herein means water-immiscible amine, with a total of at least 20 carbon atoms on its chains. Said patents teach that such amine-based extractants (ABE) lose much of their extraction efficiency upon temperature elevation. This loss of efficiency is referred to as "temperature sensitivity of extraction" (TS). The magnitude of this TS can be represented by the ratio of the distribution coefficient at the lower temperature ($D_{T1}$) to the distribution coefficient at the higher temperature ($D_{T2}$). High TS provides for the purification and the concentration of carboxylic acids through altering the temperature between extraction and back-extraction. The acid is extracted from a feed solution by an ABE at low temperature, and is then stripped or back-extracted with water at an elevated temperature. The aqueous solution obtained from that back-extraction is, in many cases, more concentrated than in the feed solution. This process is referred to herein as the "temperature swing process" (TSP). The attraction of such processes is in the fact that the sole energy consumption is that of sensible heat, which avoids the undesirable use of chemical energy as a driving force for concentrating the product and saves a lot of the latent heat of water evaporation in the final concentration.

As explained in U.S. Pat. No. 4,275,234:

"The concepts of "lower temperature" and "higher temperature" are not understood in absolute terms. What matters . . . is the temperature differential. This will have to be at least 20 degrees (centigrade), both for operation convenience and in order to make both the extraction and the back-extraction as complete as possible. The extraction may be carried out at temperatures as low as near the freezing point of the aqueous acid solution and the temperature of the back-extraction may be at or near the boiling point of the extract or the water at atmospheric pressure, or if the back-extraction is carried out under elevated pressure, at an even higher temperature, always on condition that the temperature and pressure are so chosen that the amine remains in the organic phase. In many cases the extraction can be carried out at or near room temperature, and the stripping operation at a temperature of about 20 to 40 degrees (Centigrade) above room temperature. As a rule, the stripping operation is the more effective, the higher the stripping temperature, but the extraction and stripping temperatures will be selected in individual cases in accordance with practical factors, such as corrosion-resistance and the costs of the equipment, costs of heating and cooling of the streams of the acid solution, the extract and the extractant, the required concentration of stripped acid, etc.

"If the aqueous liquid used for stripping the extract is water, the back-extract is an aqueous solution of the free acid. If desired, the back-extracting operation may be so conducted that the back-extract is an aqueous solution of a salt of the extracted acid. For example, back-extraction with an aqueous alkali metal (in this context "alkali metal" includes ammonium) hydroxide solution yields an aqueous solution of the corresponding alkali metal salt of the extracted acid. Or the aqueous back-extracting liquid may be, for example, an alkali metal chloride solution. In this case, too, the back-extract contains the corresponding alkali metal salt of the extracted acid while the amine in the extractant is converted into its hydrochloride. This will thus have to be decomposed, e.g. by treatment with calcium hydroxide, for reconstituting the extractant. Sometimes it is advantageous to perform first a back-extraction with water in order to recover the major part of the acid in the free state. The residue of acid remaining in the solvent extract can then be back-extracted with an alkali metal hydroxide or salt solution.

"The most favorable selection of the temperature of the extracting operation and of the compositions of the extractant, as regards both the amine and the solvent, will also be determined according to the given condition of particular cases, e.g., the kind of acid, its concentration in the original aqueous solution, the impurities present in that solution. The major aim in both the extracting and stripping operations will be to achieve as favorable a distribution coefficent as possible for the distribution of the acid between the aqueous and organic phases. In the extraction operation, this has to be in favor of the extractant; in the stripping operation, in favor of the aqueous phase."

As stated above, the characterizing feature of said patents is that back-extraction is performed at a temperature higher than that of the extraction. For certain acids, there is shown efficient extraction at about room temperature. Back-extraction at about 100° C. provides for a back extract, the concentration of which is similar to, or even higher than, that of the feed. In fact, a major part of citric acid production in the world is based on this process, using tridodecyl amine as the primary extractant and 1-octanol as the enhancer [Kirk-Othmer, *Encyclopedia of Chemical Technology*, 4th Ed., Vol. 6, p. 364].

The degree of product concentration in the TSP (the uphill pumping effect) depends strongly on the magnitude of the TS. The thermodynamic explanation for the TS is not clear enough. One could suggest that as the extraction process is exothermic, equilibrium is shifted backwards on temperature elevation. That would, however, be too simplistic. Thus, the most exothermic extraction is that of strong mineral acids, but no TS is found for their extraction. To the best of our knowledge, this complex phenomenon was not fully explained in said patents, and no tools were provided for predicting the magnitude of TS from the structure of the extracted acid.

The magnitude of the TS for extraction of various carboxylic acids by an extractant composed of 0.5 mol/kg trilauryl amine (Henkels Alamine 304) and 10% octanol in a kerosenic diluent have now been tested. The results are presented below in Table 1:

TABLE 1

The temperature sensitivity of carboxylic acid extraction by 0.5 mol/kg Alamine 304 + 10% octanol in kerosene.
The temperature sensitivity (TS) is presented as the distribution coefficient at 30° C., divided by that at 75° C., at various equilibrium aqueous phase concentrations.

| | | TS in Equilibrium with Aqueous Solutions of (mol/kg) | | | |
|---|---|---|---|---|---|
| Acid | pKa | 0.05 | 0.2 | 0.3 | 0.475 |
| Maleic[2] | 1.93 | 1.1 | 1.0 | 1.0 | 1.0 |
| Oxoglutaric[2] | 2.57 | 2.4 | 1.5 | 1.3 | 1.1 |
| Malonic[2] | 2.83 | 3.6 | 1.5 | 1.3 | 1.1 |
| Tartaric[2] | 3.01 | 3.4 | 3.2 | 2.7 | 2.4 |

TABLE 1-continued

The temperature sensitivity of carboxylic acid extraction by 0.5 mol/kg Alamine 304 + 10% octanol in kerosene.
The temperature sensitivity (TS) is presented as the distribution coefficient at 30° C., divided by that at 75° C., at various equilibrium aqueous phase concentrations.

| | | TS in Equilibrium with Aqueous Solutions of (mol/kg) | | | |
|---|---|---|---|---|---|
| Acid | pKa | 0.05 | 0.2 | 0.3 | 0.475 |
| Citric[3] | 3.13 | 6.0 | 3.1 | 2.6 | 2.2 |
| Malic[2] | 3.22 | 4.0 | 4.3 | 4.0 | 4.0 |
| Gluconic[2] | 3.75 | 2.1 | 2.3 | 2.4 | 2.6 |
| Lactic[1] | 3.86 | 2.5 | 2.4 | 2.4 | 2.2 |
| Succinic[2] | 4.2 | 4.3 | 4.0 | 4.0 | 4.1 |
| Glutaric[2] | 4.4 | 3.9 | 4.5 | 4.5 | 4.4 |
| Acetic[1] | 4.76 | 2.3 | 2.4 | 2.4 | 2.4 |
| Butyric[1] | 4.81 | 2.1 | 2.0 | 2.0 | 1.8 |
| Isobutyric[1] | 4.84 | 1.9 | 1.5 | 1.4 | 1.1 |
| Propionic[1] | 4.87 | 1.7 | 1.5 | 1.3 | 1.1 |

[1]Monocarboxylic acid
[2]Dicarboxylic acid
[3]Tricarboxylic acid

One can see that the TS may depend on the equilibrium concentration of the acid in the aqueous phase and that it varies significantly from one acid to the other. No linear correlation is found, however, between the TS and the strength of the acid or another defined characteristic thereof. The strongest TS was found for citric acid at the low concentration of 0.05 mol/kg; some dicarboxylic acids show a higher TS than their monocarboxylic analogues. That might indicate a tendency of TS to increase with an increase in the number of carboxylic groups. Isolating this parameter from the others is difficult.

Extraction of strong mineral acids by ABE is very efficient, reaching stoichiometric levels already at equilibrium with dilute aqueous solutions. That is true even for the weakest straight chain aliphatic amines, the tertiary ones reaching the stoichiometric extraction of 1 mol of HCl per mol of amine in equilibrium with aqueous solutions of about 0.5%. High efficiency is also found in extracting strong carboxylic acids having a pKa less than 2.5. The efficiency is, however, much lower on extracting weaker carboxylic acids by tertiary amines in a kerosenic diluent. Said low efficiency is particularly pronounced in the low concentration range. In order to avoid low yields of extraction, extraction enhancers are introduced into the extractant.

It is well-known that polar and protic compounds provide for enhancement of acid extraction by amines. These compounds may act as acid extractants by themselves, but are much weaker extractants than the amines. Extractants comprising amines and enhancers show synergistic effects in most cases, i.e., acid extraction by such extractants is much higher than the added contribution of the components.

In the description of the invention herein, and to avoid confusion, the term "primary extractant" will be used for long-chain amines used for extractions, and the term "enhancer" will be used for polar and protic extractant components, the extraction power of which is smaller than that of the primary extractant. Suitable enhancers are polar, and preferably protic compounds, including alkanols, ketones, aldehydes, esters and ethers of various molecular weights.

Desired extractants should provide high efficiency in extraction (relatively low extractant volumes, a small number of extractant stages and high yields), high selectivity, low water miscibility, low toxicity (particularly for food grade products), and efficient stripping of the extracted acid from the extract. The acid can be removed from the extract through interaction with an aqueous solution of a base to form its salt. In most cases, however, the acid is the required product rather than the salt, and acid recovery from the extract is performed by back-extraction (also termed stripping) with water or by distillation, where feasible.

As is known, high efficiency in extraction from the feed and high efficiency in stripping are conflicting requirements. Back-extraction of the extracted acid from a strong extractant requires high volumes of water and results in a very dilute aqueous solution of the acid (back-extract). The high cost of product concentration may make the whole process impractical. Distillation from a strong extractant requires high temperatures and may result in the decomposition of the acid and/or the extractant.

Extraction enhancers are polar and, preferably, protic compounds that have very low extraction capacity on their own, but significantly improve the extraction efficiency of ABE. The enhancement is explained by stabilization through salvation of the amine-acid ion pair. Octanol is used as an enhancer in the industrial TSP for production of citric acid.

Extraction enhancers have, however, an adverse effect on TSP, as the temperature sensitivity decreases with an increase in enhancer content. Such an effect is shown below in Table 2:

TABLE 2

The dependence of the temperature sensitivity of citric acid extraction by amine-based extractant Alamine 304 produced by Henkel, wherein the solvent is kerosene, on amine concentration, enhancer (octanol) concentration, and on equilibrium aqueous phase concentration. The temperature sensitivity is presented as the ratio of distribution coefficient at 30° C. and 75° C.).

| Amine mol/kg | Octanol mol/kg | D30/D75 for Citric Acid concentrations in aqueous solution at Equilibrum | | |
|---|---|---|---|---|
| | | 0.02 mol/kg | 0.5 mol/kg | 1.5 mol/kg |
| 0.2 | 0.31 | 30.0 | 6.4 | 2.1 |
| 0.2 | 0.62 | 10.8 | 2.0 | 1.3 |
| 0.2 | 2.0 | 4.9 | 1.3 | 1.1 |
| 0.5 | 0.31 | 31.3 | 3.7 | 1.4 |
| 0.5 | 0.62 | 4.6 | 1.5 | 1.1 |
| 0.5 | 2.0 | 2.1 | 1.1 | 1.05 |
| 1.0 | 0.31 | 10.5 | 1.2 | 1.07 |
| 1.0 | 0.62 | 4.9 | 1.1 | 1.01 |
| 1.0 | 2.0 | 1.8 | 1.08 | 1.03 |

There is, therefore, a trade-off between extraction efficiency and the magnitude of the TS. Thus, aiming at a higher degree of product concentration in the process leads to lower efficiency, particularly at the low concentration end, resulting in lower recovery yields, i.e., higher product losses. The absolute losses, expressed, for example, by the product concentration in the raffinate, depend on the shape of the distribution curve at the low concentration end. The proportional loss is mainly determined by the concentration of the acid in the fermentation liquor.

The TSP was implemented for citric acid recovery from fermentation liquors due to the unique, favorable combination of very high temperature sensitivity (the highest reported so far) and the relatively very high concentration of citric acid in the fermentation liquor, typically 16–18%. Even at these unique conditions, the enhancer level should be reduced to a minimum. R. Wennerstern [*J. Chem. Tech. Biotec.*, No. 33B, pp. 85–94 (1983)] studied the effect of the various extractant parameters and concluded that hydrocarbons are the preferred diluents, as polar diluents reduce the temperature effect. Cooling below ambient temperature or preconcentration of the fermentation liquor [U.S. Pat. No. 4,994,609] are required to avoid major product losses.

The above limitations brought Bauer, et al. to conclude, in 1989, that a TSP is not even economic for citric acid, and that displacement of the extracted acid by another acid (acetic) is preferable [Bauer, et al., *Ber. Bunsenges. Phys. Chem.*, Vol. 93, pp. 980–984 (1989)].

It is important to note at this juncture that ascorbic acid does not carry a carboxyl group and therefore it is not a carboxylic acid, nor is it a mineral acid. Consequently, patents and disclosures which are directed to processes for treating or recovering carboxylic and/or mineral acids do not include ascorbic acid within their scope.

According to its pKa, ascorbic acid is quite weak, being more than an order of magnitude weaker than citric acid. Its low acidity and high hydrophilicity (since it carries 4 hydroxyl groups) reduce its extraction efficiency. The same is also true for transfer of ascorbate anion.

Extraction efficiency is determined by the distribution coefficient dependence on the aqueous phase concentration (the shape of the distribution curve). The distribution coefficient at the high concentrationend determines the maximal loading of the extractant, and thereby, the volume of the extractant in the process. The distribution coefficient at the low concentration end determines the ability to approach complete extraction, and thereby, the extraction yield. For extraction of a component from a dilute feed, the yield of extraction is very important. Reaching high yields in extracting from a dilute feed a relatively weak and highly hydrophilic acid, such as ascorbic acid, would require high enhancer levels.

The present invention may not have a step in which ascorbic acid as such is extracted from solutions containing it. Yet, the aforementioned teaching regarding the effects of the various parameters on the efficiency of extraction is applicable to the effect of those parameters on the efficiency of the conversion. Thus extractant compositions of higher enhancer content would lead to lower extractant volumes and higher yields of recovery, particularly in those cases where the precursor concentration is relatively low. Such high efficiency is in conflict with high efficiency of stripping, and therefore leads to more dilute back-extract and vice versa, aiming at a higher degree of product concentration in the process leads to lower conversion efficiency, resulting in lower recovery yields. In the same way, those properties of ascorbic acid that reduce its extraction are expected to reduce the efficiency of its conversion. Distribution coefficients, for the case of the conversion step in the present invention would be considered the ratio between the concentration of ascorbic acid in the extractant and the total concentration of precursor in the feed.

Even if ascorbic acid extraction had the temperature sensitivity of citric acid extraction, one would not consider using amine-based extractants in the conversion step. That is due to the fact that at a low enhancer level in the extractant, the loss of precursor to the remaining aqueous solution would be extremely high. That is particularly true for those cases wherein the precursor is an ascorbate salt and the cation containing compound formed is basic. (Differently put, at low enhancer levels the preferred direction of the reaction would be the reaction of the acid in the extractant with said basic compound to reform the ascorbate salt). On the other hand, at high enhancer levels, the temperature sensitivity decreases, which would not allow sufficiently high product concentration in the back-extract.

In light of the above, it was extremely surprising to discover that the temperature sensitivity of ascorbic acid extraction by amine-based extractants is very high and is maintained, even at high enhancer levels. Based on this discovery, there is now provided, according to the present invention, a process for the recovery of ascorbic acid from a feed containing at least one precursor of ascorbic acid comprising converting said precursor into at least one product, said at least one product being ascorbic acid in an organic extractant composition, said organic extractant composition comprising (a) at least one secondary or tertiary alkyl amine in which the aggregate number of carbon atoms is at least 20, as a primary extractant, and (b) a polar extraction enhancer compound, wherein said extractant composition comprises at least 2 moles of said polar extraction enhancer compound per one mole of primary extractant, and subjecting said ascorbic acid-containing organic extractant composition to a stripping operation with aqueous solution at a temperature of at least 20° C. higher than the temperature at which said conversion is carried out, whereby there is obtained an aqueous solution of ascorbic acid in which the concentration of ascorbic acid is higher than 5%.

In a preferred embodiment of the present invention said precursor is a salt of ascorbic acid, preferrably an ammonium, or an alkali or an alkaline earth salt and there is provided a process for the recovery of ascorbic acid from an aqueous feed solution containing at least one salt of ascorbic acid comprising converting said salt into at least two components, a first of said components comprising a compound of the cation of said salt, and a second of said components comprising ascorbic acid in an organic extractant composition comprising (a) at least one secondary or tertiary alkyl amine in which the aggregate number of carbon atoms is at least 20, as a primary extractant, and (b) a polar extraction enhancer compound wherein said extractant composition comprises at least 2 moles of said polar extraction enhancer compound per one mole of primary extractant separating said ascorbic acid-containing organic extractant composition from residual aqueous solution; and subjecting said ascorbic acid-containing organic extractant composition to a stripping operation with aqueous solution at a temperature of at least 20° C. higher than the temperature at which said conversion is carried out whereby there is obtained an aqueous solution of ascorbic acid in which the concentration of ascorbic acid is higher than 5%.

Extractants comprising relatively strong amines as the primary extractant, show nearly no temperature sensitivity on the efficiency of extracting strong mineral acids. It was, however, found that relatively weak amines do show such effect. An example of such weak amines is the sterically-hindered, branched chain amines with branching on a carbon close to the nitrogen atom [Eyal, et. al., *Solvent Extraction and Ion Exchange*, Vol. 9, pp. 195–236 (1991)]. These amines are weaker by more than two orders of magnitude than straight chain amines, and weaker than branched chain amines with branching far from the nitrogen atom. Such amines are too weak to extract most weak acids and are not suitable for use as primary extractants in the present invention. For simplicity of language, the term "branched chain amines" will be used here just for sterically hindered, relatively weak amines with branching close to the nitrogen atom.

Branched chain amines are too weak to extract many of the carboxylic acids, particularly hydroxycarboxylic acids. Straight chain amines are much more efficient, but high conversion yield requires the use of extraction enhancer. This is particularly true for dilute feed solutions. Yet, the stronger is the enhancer and the higher its contents, the lower is the sensitivity of extraction efficiency to temperature. Thus, amine-based extractants, comprising relatively strong enhancers at high proportions of enhancers, show high efficiency in conversion, but lose most of the advantage in back-extraction at higher temperature, according to U.S. Pat. No. 4,275,234.

According to the known practice, there have been suggested four main options for the case of phosphoric acid and carboxylic acids extraction, as well as variations and combinations thereof:

a) Use of a weak enhancer or a strong enhancer, at a minimal concentration required for extraction completion (non-optimal extractant composition in extraction, high extractant volume, many stages in extraction and relatively high losses). This option was chosen for the citric acid production.

b) Increase the temperature span between extraction and back-extraction (expensive cooling and high viscosity in extraction, and expensive heating and thermal degradation in back-extraction wherein ascorbic acid is particularly sensitive to said degradation).

c) Distill at least part of the enhancer from the extract prior to back-extraction (high energy cost, limitation to volatile enhancers that in most cases have relatively high solubility in the aqueous streams, requiring additional recovery operations).

d) Add to the extract an a-polar solvent that acts as extraction suppresser, and removal of this solvent prior to the use of the regenerated extractant (low efficiency, high energy cost).

In contradistinction to the above options, a further preferred aspect of the present invention is based on the discovery that polar organic compounds with steric hindrance of the polar group have, at about ambient temperature, an enhancement effect similar to that of similar non-hindered compounds, but lower enhancement effect at elevated temperature. As a result, efficient converstion is achievable using amine-based extractants at about ambient temperature, in combination with convenient amounts of enhancer, while efficient back-extraction is achieved at elevated temperature, without resorting to unduly high temperatures in back-extraction and/or high energy-consuming removal of extractant components, either prior to back-extraction or after it.

In light of the above, there is now provided, according to preferred embodiments of the present invention, a process according to the present invention for the recovery of ascorbic acid from a feed containing at least one precursor of ascorbic acid, as hereinbefore defined comprising converting said precursor into at least one product, said at least one product being ascorbic acid in an organic extractant composition, said organic extractant composition comprising (a) at least one secondary or tertiary alkyl amine in which the aggregate number of carbon atoms is at least 20, as a primary extractant, and (b) a sterically hindered, polar, organic, extraction enhancer compound having at least 5 carbon atoms, a basicity weaker than that of said primary extractant, and temperature-sensitive, extraction-enhancing properties wherein said extractant composition comprises at least 2 moles of said extraction enhancer compound per one mole of primary extractant and subjecting said ascorbic acid-containing organic extractant composition to a stripping operation with aqueous solution at a temperature of at least 20° C. higher than the temperature at which said conversion is carried out wherein said extraction enhancer compound both enhances the extracting power of said primary extractant composition and facilitates said temperature-sensitive stripping operation, and whereby there is obtained an aqueous solution of ascorbic acid in which the concentration of ascorbic acid is higher than 5%.

In an especially preferred embodiment of the present invention said precursor is a salt of ascorbic acid, preferrably an ammonium, or an alkali or an alkaline earth salt and there is provided a process for the recovery of ascorbic acid from an aqueous feed solution containing at least one salt of ascorbic acid, comprising converting said salt into at least two components: (i) a compound of the cation of said salt and (ii) ascorbic acid in an organic extractant composition comprising (a) at least one secondary or tertiary alkyl amine in which the aggregate number of carbon atoms is at least 20, as a primary extractant, and (b) a sterically hindered, polar, organic, extraction enhancer compound having at least 5 carbon atoms, a basicity weaker than that of said primary extractant, and temperature-sensitive, extraction-enhancing properties; wherein said extractant composition comprises at least 2 moles of said extraction enhancer compound per one mole of primary extractant; separating said ascorbic acid-containing organic extractant composition from residual aqueous solution, and subjecting said ascorbic acid-containing organic extractant composition to a stripping operation with aqueous solution at a temperature of at least 20° C. higher than the temperature at which said conversion is carried out; wherein said extraction enhancer compound both enhances the extracting power of said primary extractant composition and facilitates said temperature-sensitive stripping operation, and whereby there is obtained an aqueous solution of ascorbic acid in which the concentration of ascorbic acid is higher than 5%.

In said preferred embodiments of the present invention, said sterically hindered, polar, organic extraction enhancer compound is preferably selected from the group consisting of alkanols, carboxylic acids, tertiary amines, or trialkylphosphates, having a sterically hindering substituent attached to the carbon carrying said polar group, or to a carbon which is alpha, beta, or gamma to said carbon.

Polar, and particularly protic, organic compounds act as enhancers of acid extraction by amines, due to their ability to solvate the amine acid ion pair formed on such extraction. Organic compounds suitable for use as enhancers in the present invention have at least one such polar or protic group, the solvating properties of which are hindered by the structure of the molecule. The polar group is preferably a hydroxyl, an ester, an aldehyde, a carboxyl, a ketone, or an amine, or said polar group can comprise a halogen, sulfur, nitrogen or phosphate atom. The hindrance can be achieved through substitution of a hydrogen atom in the alkyl chain by an aliphatic group, i.e., branching on the carbon atom carrying the polar group, or on a carbon which is alpha, beta, or gamma to said carbon.

The enhancer should be a weaker base than the amine used as the primary extractant in the extractant composite. On equilibrating it with a 0.1M aqueous HCl solution in a proportion that provides for enhancer to HCl molar ratio of 2, the aqueous phase pH will remain below 2. On a similar equilibration, with the amine acting by itself as the non-enhanced extractant, the pH of the aqueous phase increases to about 2.5 or higher.

In addition to the primary extractant and the sterically-hindered, polar, organic enhancer compound, the extractant may comprise a water-immiscible, polar or non-polar solvent, for example, aliphatic or aromatic hydrocarbon, hydrocarbons carrying nitro or halo substituents, and alcohols.

In preferred embodiments of the present invention, said sterically hindered, polar, extraction-enhancing compound is selected from the group consisting of secondary or tertiary alkanols, tris-2-ethylhexyl amine, and tris-2-ethylhexyl phosphate.

The present invention also provides an extractant composition for use in a process for the recovery of ascorbic acid from a feed containing at least one precursor of ascorbic acid, said composition comprising (a) at least one secondary or tertiary alkyl amine, in which the aggregate number of carbon atoms is at least 20, as a primary extractant; and (b) a sterically-hindered, polar, organic extraction enhancer compound having at least 5 carbon atoms, a basicity weaker than that of said primary extractant, and temperature-sensitive, extraction-enhancing properties.

In preferred embodiments of the present invention, said extraction composition comprises at least 3 moles of said polar extraction enhancer compound per one mole of primary extractant.

In especially preferred embodiments of the present invention, said stripping action effects the back-extraction of at least 80% of the ascorbic acid contained in said organic extractant composition.

In U.S. Pat. No. 5,041,563 and EP 133,493 an amine is used as a catalyst in the conversion of 2-ketogulonic acid ester to ascorbic acid and the amine salt of the product is formed. The next step is "cleaving the resulting ascorbic acid amine salt by liquid—liquid extraction such that the ascorbic acid is recovered in the polar phase and the amine is recovered in the non-polar phase". One way suggested for doing that, referred to as liquid—liquid extraction; is the addition of water/polar solvent and a non-polar solvent to effect distribution of the acid into the first and the amine to the latter. In certain cases an alternative, referred to as digestion, is heating with a suitable organic solvent, whereby the amine transfers into that solvent and ascorbic acid crystallizes cut. Back extraction at a temperature higher than that of extraction is not taught in these publications and thus said references also do not teach or suggest the process of the present invention. Furthermore, while the same ascorbic acid precursor is used and an amine and a solvent that could be considered as an extraction enhancer are present in the conversion step described therein, that solvent is removed from the reaction mixture prior to the recovery step and replaced by another solvent, which is a non-polar one and which therefore is not acting as an enhancer, but instead as an extractant suppressor.

U.S. Pat. Nos. 2,160,621 and 5,041,563 both disclose a process for the production of acids from the family of ascorbic acid, using an amine as a catalyst. Said patents do not teach the separation and purification of the product and therefore obviously do not teach extraction and back-extraction in the presence of an extraction enhancer and the utilization of the temperature effect of the present invention.

U.S. Pat. No. 2,443,487 discloses a method for the production of ascorbic acid, in which an amine is used as a catalyst. The amines specified are water-soluble and therefore do not provide a means of separating ascorbic acid. The product, according to said patent, is reacted with sodium hydroxide to displace the amine and sodium ascorbate is crystallized. Thus, this patent also does not teach extraction and back-extraction in the presence of an extraction enhancer and the utilization of the temperature effect of the present invention.

U.S. Pat. No. 4,778,902 teaches a method for the removal of a water-soluble amine used as a surfactant in the production of ascorbic acid. The amine is removed from the reaction mixture by adsorption on activated carbon. Similarly, Japanese 48-15931 and U.S. Pat. No. 5,637,734 teach the use of an amine as a surfactant in the production of ascorbic acid. None of said patents alone, or in combination, teach extraction and back-extraction in the presence of an extraction enhancer and the utilization of the temperature effect of the present invention.

As will be described and exemplified hereinafter, one of the major advantages of the process of the present invention for the recovery of ascorbic acid is that, after said stripping operation, the remaining organic extractant composition can be recycled, and further conversion carried out with said recycled organic extractant composition provides yields of at least 90%, and preferably at least 95%.

In most cases at least part of the product is desired in free acid form. In those cases water should be used as said aqueous solution in said stripping operation. When a part of the product is desired in a free acid form and another part of it in a form of a metal ion salt, part of the part of the ascorbic acid in the organic extractant composition is stripped with water and another part with a solution comprising a base or a salt of said metal ion. In a preferred embodiment a solution comprising a base of the metal ion is used. Preferable the base is selected from a group consisting of hydroxides, bicarbonates, carbonates and mixtures thereof. More preferably said metal ion is an alkali metal ion, most preferably sodium.

It was found that in those cases where a part of the product is desired in a free acid form and another part in a form of a metal ion salt, a preferred combined process involves first stripping ascorbic acid in acid form at the desired proportion by stripping with water and then stripping the rest with a solution comprising a base of the metal ion. Such a combination makes the stripping with water more efficient. Thus, the temperature span between the conversion temperature and that of the stripping temperature could be smaller than in the case where all the extracted acid is stripped with water. Alternatively, the same temperaturespan is used and the product of stripping with water is more concentrated. In such a preferred embodiment said stripping with a solution comprising a base of the metal ion can be effected at any convenient temperature, which does not need to be higher than that of extraction.

In a preferred embodiment of the case in which said precursor is a salt of ascorbic acid a water soluble acid is used as an acidulant in the conversion step, making use of the high selectivity of the extractants used. Preferably said water soluble acid is of acidity similar to that of ascorbic acid or weaker. Thus, an acid less preferred by the extractant than ascorbic acid (HX) is added to the solution consisting of said erythorbate salt. On contacting with the extract, ascorbic acid transfers into the extractant and a salt of HX is formed. Alternatively, HX is introduced with the extractant.

In a further preferred embodiment, of the case in which said precursor is a salt of ascorbic acid, HX is added through a membrane rather than directly. Thus said conversion step is conducted in a unit consisting of at least two compartments separated by a cation exchange membrane. At least one compartment containes said ascorbate salt solution and said organic extractant composition and at least one neighboring compartment contains a solution of HX. In the conversion step cations of said ascorbate salt are transferred through the membraneto the aqueous solution of HX, forming a salt of HX therein. In order to maintain electronutrality, protons from the aqueous solution of HX are transferred to the other compartment and are extracted along with ascorbate anions, to form an ascorbic acid containing orgainc extractant composition.

In a further preferred embodiment, of the case in which said precursor is a salt of ascorbic acid, a solution, preferably an aqueous solution, of said salt is contacted with said extractant composition in the presence of $CO_2$, preferably under pressure of at least 10 atmospheres. A conversion takes place, resulting in a carbonate or bicarbonate of the cation of said ascorbate salt and in said ascorbic acid containing organic extractant composition.

In a preferred embodiment the precursor of ascorbic acid present in said feed is a product of fermentation. In a further preferred embodiment the feed is an aqueous solution and in a further preferred embodiment said solution is a fermentation liquor. Such fermentation liquor is preferably treated prior to the extraction process. Preferably such pretreatment consists of operations such as removal of biomass by methods known per se, e.g. centrifugation, filtration and membrane filtration. If desired, the solution is treated by an adsorbent such as an active carbon, diatomaceous earth or an adsorbing resin. Other pretreatments include ion exchange, solvent extraction, etc.

In another preferred embodiment the aqueous feed is formed in an extractive fermentation. A solution out of the fermentor is said feed to the process of the present invention and said residual aqueous solution is recycled to the fermenter, as is or after some treatment. In another preferred embodiment the precursor in said solution out of the fermentor is adsorbed, preferably on a basic resin or extracted, preferably by a basic extractant. The basicity of those could be relatively high, if needed for efficient removal of the precursor from the solution, which is then recycled to the fermentor, as is or after some treatment. The adsorbed or extracted acid is stripped, preferably with a solution of a base to form a solution of a precursor, e.g. a solution of an ascorbate salt, which forms the aqueous feed in the present invention, as is or after adjustment.

In the main industrial route for the production of ascorbic acid, glucose is converted in several steps to 2-keto-L-gulonic acid, which is then converted to ascorbic acid (Reichstein and Grussner, Helv. Chim. Acta, 17, 311–328 (1934). Thus, 2-keto-L-gulonic acid forms a precursor for the production of ascobic acid.

In the Reichstein and Grussner process L-ascorbic acid is obtained by heating 2-keto-L-gulonic acid in water at 100° C. or by esterifying and treatment with sodium methoxide in methanol, followed by acidification. Yodice in WO 87/000839, assigned to the Lubrizol Corp. suggests a method for producing L-ascorbic acid comprising: forming a substantially anhydrous slurry of 2-keto-L-gulonic acid and a surfactant in a supporting organic layer and reacting said slurry with substantially anhydrous hydrogen chloride gas acid catalyst at a temperature from about 40° C. to about 80° C. for about 5 hours to convert said 2-keto-L-guionic acid to ascorbic acid.

According to the present invention a feed containing 2-keto-L-gulonic acid, a derivative thereof or a mixture thereof as a precursor is converted, preferably in the presence of a catalyst, preferably an acid, to form ascorbic acid in said organic phase composition. Said feed could consist of 2-keto-L-gulonic acid, its derivatives (including salts thereof) or a mixture thereof, in solid form or in a solution. Said solution could be an aqueous solution of it, e.g. of the kind formed by fermentation (such solution could be a fermentation liquor, a pretreated fermentation liquor, etc.) or a solution in an organic medium. Such solution in an organic medium could be formed by contacting said solid or aqueous solution with suitable organic medium. Preferably said organic medium is the organic extractant composition specified for the present invention. Thus, in a preferred embodiment 2-keto-L-gulonic acid or a derivative thereof in solid form or in an aqueous solution is contracted with an organic extractant composition specified for the present invention, to form an extractant composition comprising said acid or derivatives thereof.

Said formed composition is converted, preferably in the presence of a catalyst to form ascorbic acid in said organic phase composition. Said catalyst is preferably a substantially anhydrous acid and could be introduced in a gas form, as a highly concentrated aqueous solution and preferably in an organic medium. Such organic medium is preferably said organic extractant composition specified for the present invention. Said preferred organic medium comprising said acid is preferably formed by introduction of an organic acid or a mineral acid into it by dissolution or by extraction. Water immiscible acids and acids stronger than ascorbic acid, when used as a catalyst, stay in the organic medium formed after said conversion, during said stripping operation with water. Thus, in a preferred embodiment an organic extractant composition, as definedabove, comprising a catalyst acid from a previuos step, is contracted with a source of 2-keto-L-gulonic acid or a derivative thereof to form said organic medium feed containing both the catalyst acid and 2-keto-L-gulonic acid or a derivative thereof. Preferably said medium is homogenous. If needed, the composition of said formed medium is adjusted, e.g. by addition or removal of water, the temperature is adjusted and said conversion is effected. At the end of said conversion said ascorbic acid containing organic extractant composition is formed and subjected to said stripping operation.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE

A laboratory cell is used, which cell is composed of two compartments of the same volume, separated with a cation exchange membrane of the type SM-2 (from Neosepta). One of the compartments is filled with a 0.1 mole/kg solution of sodium ascorbate and an extractant composition, in a weight per weight ratio of 1:2. The extractant is composed of 50% Alamine 336, Henkel's tricaprylyl amine, and 50% of 2-butyl octanol. The other compartment is filled with a 0.2 mole/kg solution of HCl. After shaking the cell for 50 hours, the concentration of ascorbic acid in the organic extractant composition was 0.2 mole/kg, representing>90% conversion of the sodium ascorbate to ascorbic acid in said extractant.

Stripping, at 80° C., an organic extractant composition containing 0.2 ascorbic acid, in counter-current stages results in an aqueous solution of ascorbic acid. The concentration of said acid in the resulting solution is nearly one mole/kg.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the recovery of ascorbic acid from a feed solution containing at least one precursor of ascorbic acid, wherein said feed solution is a fermentation liquor comprising:

converting said precursor into at least one product, said at least one product being ascorbic acid in an organic extractant composition, said organic extractant composition comprising (a) at least one secondary or tertiary alkyl amine in which the aggregate number of carbon atoms is at least 20, as a primary extractant, and (b) a polar extraction enhancer compound having at least five carbon atoms and selected from the group consisting of alkanols. ketones, aldehydes, esters, ethers, carboxylic acids, tertiary amines, and trialkylphosphates;

wherein said extractant composition comprises at least 2 moles of said polar extraction enhancer compound per one mole of primary extractant; and subjecting said ascorbic acid-containing organic extractant composition to a stripping operation with aqueous solution at a temperature of at least 20° C. higher than the temperature at which said conversion is carried out;

whereby there is obtained an aqueous solution of ascorbic acid in which the concentration of ascorbic acid is higher than 5%.

2. A process for the recovery of ascorbic acid as claimed in claim 1, wherein said precursor is a salt of ascorbic acid.

3. A process for the recovery of ascorbic acid as claimed in claim 2, wherein said salt is selected from the group consisting of an ammonium, an alkali or an alkaline earth salt.

4. A process according to claim 2 for the recovery of ascorbic acid from an aqueous feed solution containing at least one salt of ascorbic acid, wherein said feed solution is a fermentation liquor comprising:

converting said salt into at least two components, a first of said components comprising a compound of the cation of said salt, and a second of said components comprising ascorbic acid in an organic extractant composition comprising (a) at least one secondary or tertiary alkyl amine in which the aggregate number of carbon atoms is at least 20, as a primary extractant, and (b) a polar extraction enhancer compound having at least five carbon atoms and selected from the group consisting of alkanols, ketones, aldehydes, esters, ethers, carboxylic acids, tertiary amines, and trialkylphosphates, wherein said extractant composition comprises at least 2 moles of said polar extraction enhancer compound per one mole of primary extractant;

separating said ascorbic acid-containing organic extractant composition from residual aqueous solution; and subjecting said ascorbic acid-containing organic extractant composition to a stripping operation with aqueous solution at a temperature of at least 20° C. higher than the temperature at which said conversion is carried out whereby there is obtained an aqueous solution of ascorbic acid in which the concentration of ascorbic acid is higher than 5%.

5. A process for the recovery of ascorbic acid as claimed in claim 1, wherein said extractant composition comprises at least 3 moles of said extraction enhancer compound per one mole of primary extractant.

6. A process for the recovery of ascorbic acid as claimed in claim 1, wherein said stripping action effects the back-extraction of at least 80% of the ascorbic acid contained in said organic extractant composition.

7. A process for the recovery of ascorbic acid as claimed in claim 1, wherein, after said stripping operation, the remaining organic extractant composition is recycled.

8. A process for the recovery of ascorbic acid as claimed in claim 7, wherein further conversion carried out with said recycled organic extractant composition provides yields of at least 90%.

9. A process for the recovery of ascorbic acid as claimed in claim 7, wherein further conversion carried out with said recycled organic extractant composition provides yields of at least 95%.

10. A process for the recovery of ascorbic acid as claimed in claim 1, wherein said feed contains said at least one precursor at a concentration of less than 1 mole/kg.

11. A process according to claim 1 for the recovery of ascorbic acid from a feed containing at least one precursor of ascorbic acid, comprising converting said precursor into at least one product, said at least one product being ascorbic acid in an organic extractant composition, said organic extractant composition comprising:

(a) at least one secondary or tertiary alkyl amine in which the aggregate number of carbon atoms is at least 20, as a primary extractant, and (b) a sterically hindered, polar, organic, extraction enhancer compound having at least 5 carbon atoms and selected from the group consisting of alkanols, ketones, aldehydes, esters, ethers, carboxylic acids, tertiary amines, and trialkylphosphates, a basicity weaker than that of said primary extractant, and temperature-sensitive, extraction-enhancing properties;

wherein said extractant composition comprises at least 2 moles of said extraction enhancer compound per one mole of primary extractant; and subjecting said ascorbic acid-containing organic extractant composition to a stripping operation with aqueous solution at a temperature of at least 20° C. higher than the temperature at which said conversion is carried out;

wherein said extraction enhancer compound both enhances the extracting power of said primary extractant composition and facilitates said temperature-sensitive stripping operation, and whereby there is obtained an aqueous solution of ascorbic acid in which the concentration of ascorbic acid is higher than 5%.

12. A process according to claim 2 for the recovery of ascorbic acid from an aqueous feed solution containing at least one salt of ascorbic acid, wherein said feed solution is a fermentation liquor comprising:

converting said salt into at least two components: (i) a compound of the cation of said salt and (ii) ascorbic acid in an organic extractant composition comprising (a) at least one secondary or tertiary alkyl amine in which the aggregate number of carbon atoms is at least 20, as a primary extractant, and (b) a sterically hindered, polar, organic, extraction enhancer compound having at least 5 carbon atoms and selected from the group consisting of alkanols, ketones, aldehydes, esters, ethers, carboxylic acids, tertiary amines, and trialkylphosphates, a basicity weaker than that of said primary extractant, and temperature-sensitive, extraction-enhancing properties;

wherein said extractant composition comprises at least 2 moles of said extraction enhancer compound per one mole of primary extractant;

separating said ascorbic acid-containing organic extractant composition from residual aqueous solution; and subjecting said ascorbic acid-containing organic extractant composition to a stripping operation with aqueous solution at a temperature of at least 20° C. higher than the temperature at which said conversion is carried out;

wherein said extraction enhancer compound both enhances the extracting power of said primary extractant composition and facilitates said temperature-sensitive stripping operation, and whereby there is obtained an aqueous solution of ascorbic acid in which the concentration of ascorbic acid is higher than 5%.

13. A process according to claim 11, wherein said sterically hindered, polar, organic, extraction enhancer compound is selected from the group consisting of alkanols, carboxylic acids, tertiary amines, or trialkylphosphates having a sterically hindering substituent attached to the carbon carrying said polar group, or to a carbon which is alpha, beta, or gamma to said carbon.

14. A process according to claim 13, wherein said substituent is an aliphatic group.

15. A process according to claim 11, wherein said extraction enhancer compound is selected from the group consisting of secondary or tertiary alkanols, tris-2-ethylhexyl amine, and tris-2-ethylhexyl phosphate.

16. A process according to claim 1, wherein said feed containing said at least one precursor of ascorbic acid is obtained by fermentation.

17. A process for the recovery of ascorbic acid as claimed in claim 1, wherein water is used as said aqueous solution in said stripping operation.

18. A process for the recovery or ascorbic acid as claimed in claim 1, wherein erythorbic acid left in said organic extractant after said stripping operation is stripped with an aqueous solution of a base.

19. A process for the recovery of ascorbic acid as claimed in claim 18, wherein said base is selected from a group consisting of alkali metal hydroxides, bicarbonates and carbonates.

20. A process for the recovery of ascorbic acid as claimed in claim 1, wherein said precursor is selected from the group consisting of salts of ascorbic acid, 2-keto-L-gulonic acid in acid and salt form and derivatives thereof.

21. A process for the recovery of ascorbic acid as claimed in claim 2, wherein said compound of said cation of said ascorbate salt is a basic compound selected from a group consisting of hydroxides, bicarbonates and carbonates.

22. A process for the recovery of ascorbic acid as claimed in claim 2, wherein said cation of said ascorbate salt is selected from a group consisting of ammonium, sodium, potassium, magnesium and calcium.

23. A process for the recovery of ascorbic acid as claimed in claim 21, wherein said basic compound is used for stripping of ascorbic acid from said organic extractant.

24. A process for the recovery of ascorbic acid as claimed in claim 21, wherein said basic compound is used in the formation of said feed solution.

25. A process for the recovery of ascorbic acid as claimed in claim 1, wherein said fermentation liquor is pretreated prior to said extraction step.

26. A process for the recovery of ascorbic acid as claimed in claim 25, wherein said pretreatment is an operation selected from the group consisting of biomass removal and treatment with an adsorbent, ion exchanger and a solvent or mixtures thereof.

27. A process for the recovery of ascorbic acid as claimed in claim 26, wherein said biomass removal is effected by membrane filtration.

28. A process for the recovery of ascorbic acid as claimed in claim 16, wherein said feed containing said at least one precursor of ascorbic acid is obtained by extractive fermentation.

* * * * *